United States Patent [19]

Yoshizato et al.

[11] Patent Number: 4,883,487

[45] Date of Patent: Nov. 28, 1989

[54] METHOD OF PRODUCING AN ARTIFICAL SKIN

[75] Inventors: Katsutoshi Yoshizato, Ebina; Toshio Taira, Yokohama; Teruo Miyata, Tokyo, all of Japan

[73] Assignee: Koken Co., Ltd., Tokyo, Japan

[21] Appl. No.: 34,958

[22] Filed: Apr. 6, 1987

[30] Foreign Application Priority Data

Apr. 19, 1986 [JP] Japan ................................. 61-91022

[51] Int. Cl.$^4$ ............................................. A61F 2/10
[52] U.S. Cl. ...................................... 623/15; 623/66; 623/901
[58] Field of Search ...................... 128/155; 623/1, 11, 623/15, 16

[56] References Cited

U.S. PATENT DOCUMENTS

| | | | |
|---|---|---|---|
| 4,294,241 | 10/1981 | Miyana | 628/155 |
| 4,485,096 | 11/1984 | Bell | 623/16 |
| 4,495,288 | 1/1985 | Jarvis, Jr. et al. | 623/11 |

OTHER PUBLICATIONS

Bell et al., *Science* 211, 1052, (1981).
Yannis et al., *Trans. Am. Soc. Artif. Intern. Ogans.* XXVII, 19, (1981).
Gallico et al., *N. Eng. J. Med.*, 448, (1984).

*Primary Examiner*—Richard J. Apley
*Assistant Examiner*—David J. Isabella
*Attorney, Agent, or Firm*—Armstrong, Nikaido, Marmelstein, Kubovcik & Murray

[57] ABSTRACT

An artifical skin comprising an insoluble atelocollagen sheet and an epidermal cell layer cultured only on one surface of the sheet, and a method of producing the same are disclosed, which method includes the steps of: forming an insoluble atelocollagen sheet; inoculating epidermal cells only on one surface of the atelocollagen sheet; and suspending the atelocollagen sheet in a liquid culture medium to culture the epidermal cells, thereby forming an epidermal cell layer.

3 Claims, No Drawings

METHOD OF PRODUCING AN ARTIFICAL SKIN

BACKGROUND OF THE INVENTION (1) Field of the Invention

The present invention relates to an artificial skin to be transplanted on a wound skin surface such as a burned or scratched skin surface, and a method of producing the same.

(2) Brief Description of the Prior Art

Conventionally, artificial skins made of collagen and so on for a temporary wound-covering material are used in practice. On the other hand, cell-incorporating artificial skins having biocompatibility are proposed by E. Bell (Science 211, 1052 (1981)) and I. V. Yannas et al. (Science 215, 174 (1982)). However, it takes a long cell culture period (about one month) in order to obtain an artificial skin by Bell et al., and the size of an avilable artificial skin piece is limited since agarlike collagen serving as the cell carrier is soft. Because of these drawbacks, the artificial skins by Bell et al. are not to this day applied for clinical use.

Currently, a method for fast culturing cells is proposed by Gallico G. G. et al. (NEJM 311, 448–451 (1984)). According to this method, epidermal cells isolated from a skin piece are cultured using 3T3 (an established cell strain obtained from a swiss mouse subcutaneous tissue) as supporting cells, and the cultured epidermal sheet is treated by dispase and removed from the supporting cells. The sheet is applied on an ointment-coated gauze to be used for transplantation.

In this case, although the cell culture period is shortened, the supporting cells remaining in the epidermal sheet adversely affect the recipient's body. This method also has the following defects:

(1) The epidermal sheet must be removed by dispase treatment.

(2) The area of the epidermal sheet is reduced to about ¼ the original area upon removing, thus causing loss in the epidermal sheet.

(3) A carrier, such as a gauze, for the epidermal sheet is additionally required.

(4) Since only the epidermal sheet is transplanted without a dermis component, no scarring remains after healing. In the case of a critical disorder such as a deficiency in the dermis deep portion, a sufficient effect cannot be expected by this method.

OBJECTS AND SUMMARY OF THE INVENTION

Accordingly, it is an object of the present invention to provide an artificial skin which leaves no scarring after healing, and a method of producing the same without using an enzymatic treatment such as a dispase treatment.

According to the present invention, the above objects are achieved by an artificial skin comprising an insoluble atelocollagen sheet and an epidermal cell layer cultured only on one surface of the sheet, and by a method of producing an artificial skin comprising the steps of:

forming an insoluble atelocollagen sheet;

inoculating epidermal cells only on one surface of the atelocollagen sheet; and suspending the inoculated atelocollagen sheet in a liquid culture medium to culture the epidermal cells, thereby forming an epidermal cell layer.

The insoluble atelocollagen sheet used in the present invention is obtained by forming a sheet by air-drying an atelocollagen solution and treating the resulting sheet by molecular crosslinking such as ultraviolet ray irradiation or glutaraldehyde treatment. The term "atelocollagen" used herein means a collagen which is obtained by treating collagen with protease, such as pepsin, in an aqueous acid solution, such as an aqueous acetic acid, to remove telopeptides at the terminal ends of collagen molecules, and at the same time, to cleave the molecular crosslinks.

Other and further objects, features and advantages of the present invention will appear more fully from the following description.

DESCRIPTION OF THE PREFERRED EMBODIMENTS

The artificial skin according to the present invention may comprise an insoluble atelocollagen sheet having a fibroblast layer cultured on at least one surface thereof and an epidermal cell layer on the fibroblast layer.

In this case, fibroblasts obtained from the recipient's living body are preferably used.

The artificial skin according to the present invention may comprise an insoluble atelocollagen sheet having an epidermal cell layer on one surface thereof and a fibroblast layer cultured on the other surface.

The artificial skin of the present invention is prepared by the following method:

An atelocollagen solution is poured into an appropriate container, air-dried, and subjected to ultraviolet ray irradiation to form an insoluble atelocollagen sheet. Epidermal cells are inoculated only on one surface of the sheet. Alternatively, fibroblasts are cultured on at least one surface of the sheet to form a fibroblast layer, and epidermal cells are inoculated on the fibroblast layer. Subsequently, the resultant sheet is suspended in a liquid culture medium and the epidermal cells are cultured to form an epidermal cell layer, thereby producing an artificial skin of the present invention.

The atelocollagen sheet used in the method of the present invention preferably has a high permeability in order to shorten the culture period for the epidermal cells. Such an atelocollagen sheet is obtained in the following manner:

An atelocollagen solution is poured into an appropriate container and air-dried to obtain an atelocollagen sheet, and the sheet is immediately allowed to be swollen with distilled water, subjected to ultraviolet ray irradiation for 10 to 30 minutes, and air-dried. Alternatively, the same atelocollagen solution as above is air-dried to obtain an atelocollagen sheet, and the sheet is subjected to ultraviolet ray irradiation, allowed to be swollen with distilled water, and freeze-dried.

The artificial skin according to the present invention has a two- to four-layer structure similar to that of a living body. It comprises an epidermal cell layer, an atelocollagen sheet, and preferably a fibroblast layer. The epidermal cell layer corresponds to the epidermal layer of the living body, and the atelocollagen sheet or the combination of the atelocollagen sheet and the fibroblast layer correspond to the dermis layer of the living body.

In the method of the present invention, when fibroblasts are cultured on at least one surface of the atelocollagen sheet to form a fibroblast layer and thereafter epidermal cells are inoculated thereon, the culturing and multiplying of the epidermal cells is accelerated because of the adhesion effect of the fibroblast layer and the atelocollagen sheet and the epidermal cell supporting effect of the fibroblast layer. It is preferable to irradiate X-rays onto the fibroblasts before inoculating epidermal cells as needed so as to control proliferation of the fibroblasts.

The artificial skin according to the present invention has the following advantages:

(a) The supporting cells do not adversely affect the recipient's body because the fibroblasts of the recipient's body are used as the supporting cells, (b) No enzymatic treatment such as a dispase treatment is required.

(c) The area of the artificial skin is not lost during skin production because no enzymatic treatment is required.

(d) No additional supporting body is required for the epidermal sheet.

(e) When a fibroblast layer as a dermis component is incorporated, a sufficient healing effect can be obtained even for a wound with a deficiency in the dermis deep portion, and no scarring remains after healing.

The present invention will be more clearly understood with reference to the following examples; however, the examples are intended to illustrate the invention and are not to be construed to limit the scope of the invention.

EXAMPLE 1

An acidic solution containing 0.3 to 1.0% of a bovine dermis atelocollagen prepared in a germ-free manner was poured into a polystyrene mold frame (9×18×1 cm) such that the solution level is 1 to 5 mm, and was air-dried in a clean bench to form an atelocollagen sheet. The sheet was removed from the mold frame, and ultraviolet ray irradiation was performed onto the two surfaces of the sheet to crosslink the atelocollagen molecules of the sheet, i.e., to render the sheet insoluble. This sheet was cut to give a circular sheet with a diameter of 25 mm. About $1 \times 10^5$ epidermal basal cells isolated from the skin of a newborn rat were inoculated only on one surface of the circular sheet. The circular sheet was suspended in a liquid culture medium "medium 199" containing a 10% fetal bovine serum, streptomycin, and a phosphoric acid buffer, and was allowed to stand for culturing the epidermal basal cells in an incubator at a $CO_2$ concentration of 5% and a temperature of 37° C. In one week the epidermal cells covered one entire surface of the sheet. An artificial skin comprising two to three epidermal cell layers was thus obtained.

The artificial skin obtained was transplanted on the skin deficiency portion of a rat of the same type as the donor rat described above. After about three weeks the skin deficiency portion exhibited ideal healing with no skin contraction.

EXAMPLE 2

About $2 \times 10^5$ fibroblasts obtained from the newborn rat of Example 1 and were cultured to form a fibroblast layer. Subsequently, in the same procedures as in Example 1, epidermal cells were cultured on the other surface of the circular sheet. The liquid culture medium used in this example consists mainly of a mixture of an Eagle minimum essential medium (modified by Dulbecco) containing a 10% fetal bovine serum and an antibiotic, and HAM F-12 at a ratio of 3:1. The epidermal cells in this example multiplied faster than in Example 1 and covered one entire surface of the sheet in about 5 days. The artificial skin obtained in this manner was transplanted on the skin deficiency portion of a rat of the same type as the donor rat. After about three weeks the skin deficiency portion exhibited ideal healing with no skin contraction.

EXAMPLE 3

In the same procedures as in Example 2, but performing the following treatment, an atelocollagen sheet having a good permeability was obtained.

More specifically, an atelocollagen sheet obtained by air-drying an atelocollagen solution was subjected to ultraviolet ray irradiation for 10 to 30 minutes, allowed to be swollen with distilled water, and freeze-dried.

The atelocollagen sheet obtained in this manner was used to culture epidermal cells in the same procedures as in Example 2. The epidermal cells multiplied faster than in Example 2. The artificial skin of this example was thus obtained in four days.

EXAMPLE 4

About $2 \times 10^5$ fibroblasts obtained from a newborn rat were cultured on one surface of an atelocollagen sheet prepared in the same procedures as in Example 1. About $2 \times 10^5$ fibroblasts of the same type as above but irradiated with a 5,000-rad X ray were separately cultured on the other surface of the atelocollagen sheet to form a fibroblast layer. Epidermal cells were cultured on the fibroblast layer under the same conditions as in Example 2. The epidermal cells of this example multiplied faster than Example 2 and covered one entire surface of the sheet in three days. The artificial skin obtained in this manner was transplanted on the skin deficiency portion of a rat of the same type as the donor rat., The skin deficiency portion exhibited ideal healing in about two weeks with no skin contraciton.

What is claimed is:

1. A method of producing an artificial skin comprising:
   (a) pouring an acidic atelocollagen solution into a mold to a depth of 1 to 5 mm;
   (b) air-drying said poured atelocollagen solution to form a dry sheet;
   (c) cross-linking said dry sheet by ultraviolet irradiation for a time sufficient to form an insoluble atelocollagen sheet;
   (d) inoculating epidermal cells on one surface of said atelocollagen sheet; and
   (e) suspending the inoculated atelocollagen sheet in a liquid culture medium to culture said epidermal cells, thereby forming an epidermal cell layer.

2. A method according to claim 1, further comprising culturing fibroblasts on at least one surface of said insoluble altelocollagen sheet prior to inoculating with epidermal cells.

3. A method according top claim 1, wherein the concentration of atelocollagen in the poured solution is 0.3 to 1.0%.

* * * * *